United States Patent [19]

Nagy née Kricsfalussy et al.

[11] Patent Number: 5,489,615
[45] Date of Patent: Feb. 6, 1996

[54] PHARMACEUTICAL OINTMENT BEING FREE FROM SKIN IRRITATIVE ACTION AND A PROCESS FOR THE PREPARATION THEREOF

[75] Inventors: Margit Nagy née Kricsfalussy; Mária Hoór; Mária Szeli née Séger; János Egri; Rita Balázs; Márta Kovács; Gyula Sebestyén, all of Budapest; Antal Mosonyi, Körmend, all of Hungary

[73] Assignee: Egis Gyogyszergyar Rt., Budapest, Hungary

[21] Appl. No.: 171,471

[22] Filed: Dec. 22, 1993

[30] Foreign Application Priority Data

Dec. 23, 1992 [HU] Hungary ............... P 92 04104

[51] Int. Cl.$^6$ ........................... A61K 9/06
[52] U.S. Cl. .............. 514/772.4; 424/400; 424/401; 514/969
[58] Field of Search ............ 424/78.01; 514/772.4, 514/772.3

[56] References Cited

U.S. PATENT DOCUMENTS

| | | | |
|---|---|---|---|
| 4,678,666 | 7/1987 | Nozawa et al. | 424/78.05 |
| 4,944,949 | 7/1990 | Story et al. | 424/451 |
| 4,952,560 | 8/1990 | Kigasawa et al. | 514/2 |

*Primary Examiner*—Thurman K. Page
*Assistant Examiner*—P. Kulkosky
*Attorney, Agent, or Firm*—Beveridge, DeGrandi, Weilacher & Young

[57] ABSTRACT

A pharmaceutical ointment is disclosed containing to 10 percent by mass of micronized piroxicam, 15 to 30 percent by mass of hydrophobic carrier(s), 60 to 75 percent by mass of water, 0.1 to 10 percent by mass of additive(s), and 2 to 5 percent by mass of emulsifiers selected from (i) a poly(ethylene glycol) alkyl or alkenyl ether and (ii) a sorbitane ester of a fatty acid or an oleic acid in a mass ratio of 3:1 to 1:3. The ointment is free from skin irritative action and has local antiphlogistic activity. In addition, a process for preparing he pharmaceutical ointment is provided.

12 Claims, No Drawings

PHARMACEUTICAL OINTMENT BEING FREE FROM SKIN IRRITATIVE ACTION AND A PROCESS FOR THE PREPARATION THEREOF

The invention refers to a pharmaceutical ointment being free from skin irritative action and comprising 0.5 to 10 percent by mass of piroxicam, 15 to 30 percent by mass of hydrophobic carrier(s), 60 to 75 percent by mass of hydrophilic carrier(s), 0.1 to 10 percent by mass of additive(s) and emulsifiers, furthermore a process for the preparation of the ointment. The ointment of the invention has an excellent local antiphlogistic activity.

Piroxicam is the international non-proprietory name of N-(2-pyridyl)-2-methyl-4-hydroxy-2H-1,2-benzothiazine-3-carboxamide-1,1-dioxide strong antiphlogistic action (U.S. Pat. No. 3,591,584). Piroxicam can be advantageously used for the local treatment of rheumatism in the form of a pharmaceutical ointment.

Such a preparation is known from the published European Patent Application No. 101 178 according to which piroxicam is dissolved in a mixture of water, ethanol and polyol(s), and the ointment-like state is formed by a carboxyvinyl polymer used as a gel forming agent. The known preparation has the character of a gel, rather than that of an ointment, and its use is extremely detrimental to the skin surface. It has a pH value of 6.5 to 9.0, thus, in certain cases the pH of the known preparation is significantly higher than the natural pH value of the skin (i.e. 4 to 6). As indicated by the examples, the known preparation contains 25 to 40 percent by mass of ethanol dissolving the fats of the horny layer of skin. Thus, then using the known preparation, the skin surface becomes brittle. Since, in general, the skin surface is treated repeatedly for a longer time with the antiphlogistic preparation to cure the rheumatic state, serious skin irritation is often experienced due to the high ethanol content and the detrimental pH range.

A cream is known from the published European Patent Application No. 481 725 wherein the active agent is present in a mixture of water, a polyol and an alcohol of higher carbon atoms, and the stability of the composition is provided by 10 to 25 percent by mass of emulsifier. During a prolonged treatment the high emulsifier content exerts a similar drying effect on the skin surface as the ethanol content of the preparation known from the published European Patent Application No. 101 178. A further drawback of the known cream preparation resides in the fact that the originally white cream becomes yellow in a short time when stored at room temperature. This property of topical compositions containing piroxicam has been already mentioned in the published European Patent Application No. 101 178. The discolouration is attributed to the formation of a hydrate of piroxicam in the presence of moisture. This hydrate has yellow colour and reduces the absorbability of piroxicam through the skin.

Furthermore, patients come to distrust pharmaceutical compositions discolouring during the treatment.

The aim of the invention is to provide a pharmaceutical ointment comprising piroxicam as the active agent, wherein said ointment has an improved stability (i.e. it does not become yellow when stored under the usual conditions) and it is harmless to the skin even during prolonged treatment.

It has been found that the above aim is achieved by the pharmaceutical ointment of the invention comprising 0.5 to 10 percent by mass of piroxicam, 15 to 30 percent by mass of hydrophobic carrier(s), 60 to 75 percent by mass of hydrophilic carrier(s), 0.1 to 10 percent by mass of additive(s) and 2 to 5 percent by mass of emulsifiers consisting of (i) a poly(ethylene glycol) alkyl or alkenyl ether and (ii) a sorbitane ester of a fatty acid or an oleic acid in a mass ratio of 3:1 to 1:3.

The hydrophobic carriers are the usual carriers of hydrophobic character of pharmaceutical ointments such as hydrocarbons e.g. liquid paraffin or vaseline; silicones e.g. liquid poly(dimethyl siloxane); long chain saturated or unsaturated alkanols e.g. cetyl alcohol, lauryl alcohol, myristyl alcohol, stearyl alcohol or oleyl alcohol; fatty acids e.g. lauric acid, myristic acid, palmitic acid or stearic acid; esters e.g. isopropyl myristate, isopropyl palmitate or vegetable oils; ethers e.g. poly(propylene glycol); lanoline etc. or the mixtures thereof.

Preferred hydrophobic carriers are as follows: liquid paraffin, vazeline, fatty acids such as stearic acid, fatty alcohols such as cetyl stearyl alcohol etc.

Hydrophilic carriers are the usual carriers of hydrophilic character of pharmaceutical ointments such as water or organic solvents being miscible with water e.g. alcohols, preferably polyols such as glycerol, sorbitol, propylene glycol, liquid poly(ethylene glycol) etc. or the mixtures thereof.

In the pharmaceutical ointment of the invention, a preferred hydrophilic carrier is the water.

Additives are the usual additives of pharmaceutical ointments such as structural matrix forming agents e.g. solid paraffin, ceresin, polyethylene, silicates for instance colloidal aluminium silicate or colloidal magnesium aluminium silicate, cholesterol, beewax or carnauba wax; viscosity enhancing agents e.g. colloidal silica, agar, methyl cellulose, carboxymethyl cellulose, microcrystalline cellulose or carboxyvinyl polymers; preserving agents e.g. alkyl p-hydroxybenzoate, butylhydroxytoluene, butylhydroxyanisol, benzyl alcohol, phenylethanol, sorbic acid, citric acid or a metal salt of the acids listed; antioxidants e.g. vitamine E; buffers; parfumes etc.

The emulsifier system of the invention is a mixture of two constituents in a mass ratio of 3:1 to 1:3. One of them is a poly(ethylene glycol) alkyl or alkenyl ether, preferably a poly(ethylene glycol) ($C_{10-20}$ alkyl or alkenyl) ether wherein the poly(ethylene glycol) residue consists of 2 to 23 oxyethylene groups, in general. Emulgators of this type are known under the trade name e.g. Brij(R); preferred species in the pharmaceutical ointment of the invention are as follows:

Brij(R)56: poly(ethylene glycol) cetyl ether (degree of polymerization: 10) and/or Brij(R)78: poly(ethylene glycol) stearyl ether (degree of polymerization: 20) and/or Brij(R)58: poly(ethylene glycol) cetyl ether (degree of polymerization: 20) and/or Brij(R)72: poly(ethylene glycol) stearyl ether (degree of polymerization: 2) and/or Brij(R)35: poly(ethylene glycol) lauryl ether (degree of polymerization: 23) and/or Brij(R)92: poly(ethylene glycol) oleyl ether (degree of polymerization: 2) and/or Brij(R)96: poly(ethylene glycol) oleyl ether (degree of polymerization: 10) and/or Brij(R)98: poly(ethylene glycol) oleyl ether (degree of polymerization: 20).

The other constituent of the emulsifier mixture of the invention is a sorbitane ester of a fatty acid or an oleic acid, preferably a sorbitane mono- or triester. Emulgators of this type are known under the trade name e.g. Span(R); preferred species in the pharmaceutical ointment of the invention are as follows:

Span(R)20: sorbitane monolaurate and/or

Span$^{(R)}$40: sorbitane monopalmitate and/or
Span$^{(R)}$60: sorbitane monostearate and/or
Span$^{(R)}$65: sorbitane tristearate and/or
Span$^{(R)}$80: sorbitane monooleate and/or
Span$^{(R)}$85: sorbitane trioleate.

The pharmaceutical ointment of the invention is prepared by blending at first the hydrophobic carrier(s), hydrophilic carrier(s), additives(s) and emulsifiers, then admixing piroxicam to the mixture obtained. It is preferred to employ piroxicam in a micronized form.

Preferably, one proceeds as follows:

a) in a separate step, the hydrophobic carrier(s), the sorbitane ester and the additive(s) dissolving only in the fatty phase are blended under heating at a temperature not higher than 80° C.;

b) the further additives, if any, and the poly(ethylene glycol) ether are dissolved in the hydrophilic carrier(s) under heating at a temperature generally not higher than 90° C., and the solution obtained is admixed to the fatty phase;

c) the mixture is slowly cooled while piroxicam is added, then the ointment obtained is cooled to room temperature and filled into suitable containers such as tubes.

The poly(ethylene glycol) ether constituent of the emulsifier system of the invention can be admixed to the hydrophobic carrier(s), too, together with the sorbitane ester.

It is surprising that the emulsifier system of the invention is sufficient in an amount of 2 to 5 percent by mass to produce a stable ointment since, on the basis of the published European Patent Application No. 481 725, the presence of at least 10 percent by mass of an emulsifier seems to be essential to avoid the separation of the ointment constituents.

The stability of the ointments of the invention corresponding to Examples 1 to 6 were examined by keeping them at 40° C. for 12 weeks. (This test was a so called "accelerated stability test" since pharmaceutical compositions would not be stored at about 40° C. in practice.) No discolouration or change of consistence of the ointment samples could be noted. The whole quantity of the ointment removed from the tubes remained white, and no separation was experienced, that is the ointment kept its homogeneity.

The pharmaceutical ointment of the invention corresponding to Examples 1 to 6 were stored at room temperature for more than 1 year without any reduction of stability.

It is also surprising that the pharmaceutical ointment of the invention does not irritate the skin on prolonged treatment since it was found that reference samples having essentially identical composition but comprising partly different emulsifiers strongly irritate the skin in the dermal irritation test.

In the test, mature male and female rabbits from a New Zealand stock have been used. The body weight of the animals was 2500 g±20 percent at the beginning of the test. The rabbits were kept singly in hutches at 20±3° C. and 50 to 70 percent relative humidity. The animals were fed with standard pressed food for rabbits and could drink tap water ad libitum. Before starting the test, the animals have been observed for a week: the body weights have been determined and the behaviour has been noted. Only the healthy animals having no pathological clinical symptoms were selected to the test. On the day that preceded the treatment, the dorsal skin surface of the rabbits were depilated on 3 areas each measuring 2.5 cm×3 cm. On the next day the animals were treated as follows:

In case of each test animal, one of the depilated areas of the dorsal skin surface was used as an untreated control; the other depilated area was covered with 100 mg of the ointment tested; the third depilated area was covered with 100 mg of control ointment containing no active substance i.e. piroxicam. (The latter control ointment contained water in place of piroxicam.) The same composition was tested on 6 rabbits. The skin areas treated were covered with antiseptic gauze sheets that were fastened with waterproof adhesive plasters. After 4 hours the gauze sheets were removed and any residue of the test ointment was washed down from the treated areas with physiological saline. The treatments were performed 14 times, day by day, once daily using the following compositions:

a) ointment of Example 1;
b) ointment of Example 4;
c) ointment of Example 5;
d) ointment of Example 6.

Ointments used as reference:

Their composition corresponded to that of Example 1 with the difference that instead of an 1:1 mixture of poly(ethylene glycol) cetyl ether and sorbitane monostearate the emulsifier system consisted of:

e) 2 percent by mass of poly(ethylene glycol) stearate (degree of polymerization: 3) (Myrj$^{(R)}$) and 2 percent by mass of sorbitane monostearate (Span$^{(R)}$ 60);

f) 2 percent by mass of poly(ethylene glycol) stearate (degree of polymerization: 3) (Myrj$^{(R)}$52) and 2 percent by mass of sorbitane trioleate (Span$^{(R)}$85);

g) 2 percent by mass of poly(ethylene glycol) stearate (degree of polymerization: 4) (Myrj$^{(R)}$53) and 2 percent by mass of sorbitane monostearate (Span$^{(R)}$ 60);

h) 2 percent by mass of poly(ethylene glycol) sorbitane monolaurate (Tween$^{(R)}$20 ) and 2 percent by mass of sorbitane monostearate (Span$^{(R)}$ 60);

i) 1 percent by mass of poly(ethylene glycol) stearate (degree of polymerization: 3) (Myrj$^{(R)}$52), 1.5 percent by mass of poly(ethylene glycol) cetyl ether (Brij$^{(R)}$58 and 1.5 percent by mass of sorbitane monostearate (Span$^{(R)}$60).

The changes on the dorsal skin surface of the animals or the lack of change are summarized in Table I.

TABLE I

| Dermal irritation on rabbits | |
|---|---|
| Ointment tested | Observation |
| Ointment of the invention | |
| a) | no change on the skin |
| b) | no change on the skin |
| c) | no change on the skin |
| d) | no change on the skin |
| Ointment used as reference | |
| e) | on day 3: slight erythema, on day 5: strong inflammation, on day 7: oedema; |
| f) | on day 3: slight erythema, on day 5: strong inflammation, on day 7: oedema; |
| g) | on day 3: slight erythema, on day 6: strong inflammation, on day 9: oedema; |
| h) | on day 3: slight erythema, on day 4: strong inflammation, on day 6: oedema; |
| i) | on day 4: slight erythema, on day 7: strong inflammation, on day 12: oedema. |

Notes on Table I:
No change of the skin was found in case of control ointments that corresponded to ointments a), b) and c) but contained no piroxicam.

In case of control ointments that corresponded to reference ointments d) to h) but contained no piroxicam, the symptoms of imflammation could be detected 1 or 2 days sooner than in case of the reference preparations themselves.

No change of the skin surface was detected on the areas that corresponded to the controls without treatment.

From Table I it can be seen that if the emulgators of the pharmaceutical ointments tested consist of the emulsifier system of the invention, no skin irritation is found during the treatment period of 14 days. However, if the emulgators are other than the emulsifier system of the invention, serious skin irritation can be observed. This skin irritation cannot be attributed to the presence of piroxicam since, in case of the reference control ointments, the irritation is developed at an earlier date.

Thus, the pharmaceutical ointment of the invention is free from any skin irritation and remains stable for a long time.

The invention is further elucidated by means of the following Examples.

EXAMPLE 1

A pharmaceutical ointment having the following composition is prepared:

| | |
|---|---|
| Piroxicam (micronized) | 1.0 g |
| Methyl p-hydroxybenzoate | 0.1 g |
| Brij ® 58/poly(ethylene glycol) cetyl ether/ | 2.0 g |
| Water (distilled) | 71.9 g |
| Stearic acid | 3.0 g |
| Paraffin (liquid) | 12.0 g |
| Cetyl stearyl alcohol | 3.0 g |
| Vaseline (white) | 5.0 g |
| Span ® 60 (sorbitane monostearate) | 2.0 g |
| | 100.0 g |

The white vaseline, liquid paraffin, sorbitane monostearate and cetyl stearyl alcohol are transferred into a suitable melting pot and melted at 80° C. to obtain the fatty phase. The methyl p-hydroxybenzoate and poly(ethylene glycol) cetyl ether are dissolved in the distilled water at 90° C. to obtain the aqueous phase. The aqueous phase is added in several portions to the fatty phase under constant stirring, then the mixture is slowly cooled under stirring, while the micronized piroxicam is added in portions. Having suspended the total amount of piroxicam, the ointment obtained is cooled to 25° C. and filled into tubes.

The pH value of the water shaked with a sample of the ointment obtained is equivalent to 4.43.

EXAMPLE 2

A pharmaceutical ointment having the following composition is prepared:

| | |
|---|---|
| Piroxicam (micronized) | 1.0 g |
| Methyl p-hydroxybenzoate | 0.1 g |
| Brij ® 78/poly(ethylene glycol) stearyl ether/ | 2.4 g |
| Water (distilled) | 71.9 g |
| Stearic acid | 3.0 g |
| Paraffin (liquid) | 12.0 g |
| Cetyl stearyl alcohol | 3.0 g |
| Vaseline (white) | 5.0 g |
| Span ® 85 (sorbitane trioleate) | 1.6 g |

The constituents are blended as described in Example 1 with the difference that only the methyl p-hydroxybenzoate is dissolved in the distilled water, the poly(ethylene glycol) stearyl ether is added directly to the constituents of the fatty phase before melting.

The pH value of the water shaked with a sample of the ointment obtained is equivalent to 5.36.

EXAMPLE 3

A pharmaceutical ointment having the following composition is prepared as described in Example 1:

| | |
|---|---|
| Piroxicam (micronized) | 1.0 g |
| Methyl p-hydroxybenzoate | 0.1 g |
| Brij ® 98/poly(ethylene glycol) oleyl ether/ | 2.1 g |
| Water (distilled) | 72.9 g |
| Stearic acid | 3.0 g |
| Paraffin (liquid) | 12.0 g |
| Cetyl stearyl alcohol | 3.0 g |
| Vaseline (white) | 5.0 g |
| Span ® 65 (sorbitane monostearate) | 0.9 g |
| | 100.0 g |

The pH value of the water shaked with a sample of the ointment obtained is equivalent to 4.91.

EXAMPLE 4

A pharmaceutical ointment having the following composition is prepared as described in Example 1:

| | |
|---|---|
| Piroxicam (micronized) | 10.0 g |
| Propyl p-hydroxybenzoate | 0.1 g |
| Brij ® 58/poly(ethylene glycol) lauryl ether/ | 1.5 g |
| Water (distilled) | 62.1 g |
| Stearic acid | 3.0 g |
| Paraffin (liquid) | 12.0 g |
| Cetyl stearyl alcohol | 3.0 g |
| Vaseline (white) | 5.0 g |
| Span ® 20 (sorbitane monolaurate) | 3.3 g |
| | 100.0 g |

The pH value of the water shaked with a sample of the ointment obtained is equivalent to 5.13.

EXAMPLE 5

A pharmaceutical ointment having the following composition is prepared as described in Example 1:

| | |
|---|---|
| Piroxicam (micronized) | 5.0 g |
| Methyl p-hydroxybenzoate | 0.2 g |
| Brij ® 96/poly(ethylene glycol) oleyl ether/ | 1.0 g |
| Water (distilled) | 69.8 g |
| Stearic acid | 3.0 g |
| Paraffin (liquid) | 12.0 g |
| Cetyl stearyl alcohol | 3.0 g |
| Vaseline (white) | 5.0 g |
| Span ® 40 (sorbitane monopalmitate) | 1.0 g |
| | 100.0 g |

The pH value of the water shaked with a sample of the ointment obtained is equivalent to 4.36.

EXAMPLE 6

A pharmaceutical ointment having the following composition is prepared as described in Example 1:

| | |
|---|---|
| Piroxicam (micronized) | 1.0 g |
| Methyl p-hydroxybenzoate | 0.1 g |
| Brij ® 56/poly(ethylene glycol) cetyl ether/ | 3.1 g |
| Water (distilled) | 71.5 g |
| Stearic acid | 3.0 g |
| Paraffin (liquid) | 12.0 g |
| Cetyl stearyl alcohol | 3.0 g |
| Vaseline (white) | 5.0 g |
| Span ® 80 (sorbitane monostearate) | 1.3 g |
| | 100.0 g |

The pH value of the water shaked with a sample of the ointment obtained is equivalent to 5.12.

We claim:

1. A pharmaceutical ointment, said ointment comprising 0.5 to 10 percent by mass of micronized piroxicam, 15 to 30 percent by mass of hydrophobic carrier(s), 60 to 75 percent by mass of water, 0.1 to 10 percent by mass of additive(s), and 2 to 5 percent by mass of emulsifiers consisting of (i) a poly(ethylene glycol) alkyl or alkenyl ether and (ii) a sorbitane ester of a fatty acid or an oleic acid in a mass ratio of 3:1 to 1:3, wherein said ointment is free from skin irritative action.

2. A pharmaceutical ointment as claimed in claim 1, in which the poly(ethylene glycol) alkyl or alkenyl ether contains 10 to 20 carbon atoms in the alkyl or alkenyl chain and 2 to 23 oxyethylene groups.

3. A pharmaceutical ointment as claimed in claim 2, in which the alkyl ether is acetyl, stearyl or lauryl ether.

4. A pharmaceutical ointment as claimed in claim 2, in which the alkenyl ether is an oleyl ether.

5. A pharmaceutical ointment as claimed in claim 1, in which the fatty acid is stearic or palmitic acid.

6. A process for preparing a pharmaceutical ointment, said ointment comprising 0.5 to 10 percent by mass of micronizod piroxicam, 15 to 30 percent by mass of hydrophobic carrier(s), 60 to 75 percent by mass of water, 0.1 to 10 percent by mass of additive(s), and 2 to 5 percent by mass of emulsifiers consisting of (i) a poly(ethylene glycol) alkyl or alkenyl ether and (ii) a sorbitane ester of a fatty acid or an oleic acid in a mass ratio of 3:1 to 1:3, said ointment being free from skin irritative action, said process comprising admixing 15 to 30 percent by mass of hydrophobic carrier(s), 60 to 75 percent by mass of water, 0.1 to 10 percent by mass of additive(s) and 2 to 5 percent by mass of emulsifiers consisting of (i) a poly-(ethylene glycol) alkyl or alkenyl ether and (ii) a sorbitane ester of a fatty acid or an oleic acid in a mass ratio of 3:1 to 1:3, and adding 0.5 to 10 percent by mass of micronizod piroxicam to the mixture of the above constituents.

7. The pharmaceutical ointment according to claim 1, wherein said hydrophobic carrier(s) is selected from the group consisting of liquid paraffin, fatty acids, and fatty alcohols.

8. The pharmaceutical ointment according to claim 7, wherein said fatty acid is stearic acid and said fatty alcohol is cetyl stearyl alcohol.

9. The process according to claim 6, wherein the pH of said ointment is from 4.43 to 5.36.

10. The pharmaceutical ointment according to claim 1, wherein the pH of said ointment is from 4.43 to 5.36.

11. A pharmaceutical ointment consisting essentially of 0.5 to 10 percent by mass of micronizod piroxicam, 15 to 30 percent by mass of hydrophobic carrier(s), 60 to 75 percent by mass of water, 0.1 to 10 percent by mass of additive(s), and 2 to 5 percent by mass of emulsifiers consisting of (i) a poly(ethylene glycol) alkyl or alkenyl ether and (ii) a sorbitane ester of a fatty acid or an oleic acid in a mass ratio of 3:1 to 1:3, wherein said ointment is free from skin irritative action.

12. A process for preparing a pharmaceutical ointment, said ointment consisting essentially of 0.5 to 10 percent by mass of micronized piroxicam, 15 to 30 percent by mass of hydrophobic carrier(s), 60 to 75 percent by mass of water, 0.1 to 10 percent by mass of additive(s), and 2 to 5 percent by mass of emulsifiers consisting of (i) a poly(ethylene glycol) alkyl or alkenyl ether and (ii) a sorbitane ester of a fatty acid or an oleic acid in a mass ratio of 3:1 to 1:3, said ointment being free from skin irritative action, said process consisting essentially of admixing 15 to 30 percent by mass of hydrophobic carrier(s), 60 to 75 percent by mass of water, 0.1 to 10 percent by mass of additive(s) and 2 to 5 percent by mass of emulsifiers consisting of (i) a poly-(ethylene glycol) alkyl or alkenyl ether and (ii) a sorbitane ester of a fatty acid or an oleic acid in a mass ratio of 3:1 to 1:3, and adding 0.5 to 10 percent by mass of micronized piroxicam to the mixture of the above constituents.

\* \* \* \* \*